US007670767B1

(12) United States Patent
Shayesteh et al.

(10) Patent No.: US 7,670,767 B1
(45) Date of Patent: Mar. 2, 2010

(54) GENETIC ALTERATIONS ASSOCIATED WITH CANCER

(75) Inventors: Laleh Shayesteh, Foster City, CA (US); Joe W. Gray, San Francisco, CA (US); Gordon B. Mills, Houston, TX (US); Yiling Lu, Houston, TX (US)

(73) Assignees: The Regents of the University of California, Oakland, CA (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 08/905,508

(22) Filed: Aug. 4, 1997

Related U.S. Application Data

(63) Continuation-in-part of application No. 08/837,046, filed on Apr. 5, 1997, now Pat. No. 6,110,673, which is a continuation-in-part of application No. 08/783,729, filed on Jan. 16, 1997, now Pat. No. 6,277,563.

(51) Int. Cl.
*C12Q 1/68* (2006.01)
(52) U.S. Cl. .............................................. 435/6; 514/2
(58) Field of Classification Search .................... 514/2; 435/6
See application file for complete search history.

(56) References Cited

U.S. PATENT DOCUMENTS

| 5,143,854 | A | 9/1992 | Fodor et al. .................. 436/518 |
| 5,378,725 | A | 1/1995 | Bonjouklian et al. |
| 6,632,789 | B1 * | 10/2003 | June ............................... 514/1 |

FOREIGN PATENT DOCUMENTS

| WO | WO 93/21328 | 10/1993 |
| WO | WO 93/21328 | 6/1996 |
| WO | WO 96/40713 A1 | 12/1996 |

OTHER PUBLICATIONS

Minaguchi et al. Cacner Research 59: 6063-6067, Dec. 15, 1999.*
Shayesteh et al. Nature Genetic 21(1): 99-102, Jan. 1999.*
Hu et al. Clinical Cancer Research (Mar. 2000) 6: 880-886.*
Hu et al ; Clinical Cancer Research, 2000; vol. 6, pp. 880-886.*
Fry, M.J. Breast Cancer Research; 2001, vol. 3, pp. 304-312.*
Verma et al. (1997) Nature, vol. 389, p. 239.*
Orkin et al. (1995) Report to the NIH; pp. 1-40.*
Boytim et al ; Journal of Clinical Investigation, vol. 105 pp. 1447-1453; 2000.*
Sonoda et al ; Genes, Chromosomes, and Cancer; vol. 20, pp. 320-328, 1997.*
Arnold et al; Genes, Chromosomes, and Cancer, vol. 16, pp. 46-54, 1996.*
Volinia et al; Genomics, vol. 24, pp. 472-477; 1994.*
Xiao et al; International Journal of Oncology; vol. 6, pp. 405-411, 1995.*
Skorski et al; Blood, vol. 86, pp. 726-736, 1995.*
Powis et al; International Journal of Pharmacognosy, vol. 33, pp. 17-26, 1995.*
Lavin et al; Experientia, vol. 52, pp. 979-994, 1996.*
Daneshvar et al; American Journal of Human Genetics, (1996) vol. 59, No. 4 SUPPL., pp. A65.*
F.H. Thompson et al., *Cancer Genet. Cytogenet.* (1996) 87: 55-62.
Baker, et al., Science, 244:217-21 (1989).
Brzoska, et al., Cancer Research, 15:3055-9 (1995).
Cawthon, et al., Cell, 62:193-201 (1990).
Friend, et al., Nature, 323:643-6 (1986).
Fukumoto, et al., Proc. Natl. Acad. Sci., vol. 85, pp. 5434-5438 (1988).
Iwabuchi, et al., "Genetic Analysis of Benign, Low-Grade, and High-Grade Ovarian Tumors," Cancer Research, 55:6172-6180 (Dec. 15, 1995).
Kallioniemi, et al., Science, 258:818-21 (1992).
Parker and Waterfield, Cell Growth and Differentiation, vol. 3, pp. 747-752 (1992).
Pinkel, et al., Proc. Natl. Acad. Sci. USA, vol. 85, pp. 9138-9142 (1988).
Ried, et al., Cancer Research, 54:1801-6 (1994).
Sakamoto, et al., Cytometry, vol. 19, pp. 60-69 (1995).
Serunian, et al., J. Virol., vol. 64, pp. 4718-4725 (1990).
Shuin, et al., Cancer Research, 54:2832-5 (1994).
Speicher, et al., Cancer Research, 55:1010-3 (1995).
Tsakiridis, et al., "Multiple Roles of Phosphatidylinositol 3-Kinase in Regulation of Glucose Transport, Amino Acid Transport, and Glucose Transporters in L6 Skeletal Muscle Cells," Endocrinology, vol. 136, No. 10, pp. 4315-4322 (1995).
Visalcorpi, et al., Nature Genetics, vol. 9, pp. 401-406 (1995).
Volina, et al., "Molecular Cloning, cDNA Sequence, and Chromosomal Localization of the Human Phosphatidylinositol 3_Kinase p100alpha (PEK3CA) Gene," Genomics, vol. 24, pp. 472-477, Sep. 1994.
Weinberg, Cancer, vol. 61, pp. 1963-1968 (1988).
Yamamoto, et al., "Over-expression of Facilitative Glucose Transporter Genes in Human Cancer," Biochemical and Biophysical Research Communications, vol. 170, No. 1, pp. 223-230, Jul. 16, 1990.
Brass, N, et al.: "DNA Amplification on Chromosome 3q26.1-q26.3 in Squamous Cell Carcinoma of the Lung Detected by Reverse Chromosome Painting;" *European Journal of Cancer;* 1996; pp. 1205-1208; vol. 32A; No. 7, Elsevier Science Ltd.; Great Britain.
Brass, Nicole, et al; "Translation Initiation Factor eIF-4gamma Is Encoded by an Amplified Gene and Induces an Immune Response in Squamous Cell Lung Carcinoma;" *Human Molecular Genetics*; 1997; pp. 33-39; vol. 6; No. 1; Oxford University Press.
Brooks, DJ, et al.; "Expression of the Zinc Finger Gene EVI-1 in Ovarian and Other Cancers" *British Journal of Cancer*, 1996; pp. 1518-1525; Stockton Press.

(Continued)

*Primary Examiner*—Sheela J Huff
(74) *Attorney, Agent, or Firm*—Townsend and Townsend and Crew LLP

(57) ABSTRACT

The present invention provides new probes for the detection of chromosomal alterations associated with cancer, particularly ovarian cancer. The probes bind selectively with target nucleic acid sequences at 3q26.

3 Claims, 7 Drawing Sheets

OTHER PUBLICATIONS

Daneshvar, Laleh, et al.; "Fine Mapping of a Region of Increased Copy Number In Epithelial Ovarian Cancer," *American Journal of Human Genetics*; 1996; pp. A65; vol. 59; No. 4.

Gemmill, R.M.; "A Second-generation YAC Contig Map of Human Chromosome 3;" *Genome Directory*; Sep. 28, 1995; pp. 299-319; vol. 377.

Gnatt Averell, et al.; "Expression of Alternatively Terminated Unusual Human Butyrylcholinesterase Messenger RNA Transcripts, Mapping to Chromosome 3q28-ter, in Nervous System Tumors;" *Cancer Research*; Apr. 1, 1990; pp. 1983-1987; vol. 50.

Ram Tracy, G.; et al.; "Phosphatidylinositol 3-Kinase Recruitment by $p185^{brbb2}$ and erb8-3 is Potently Induced by neu Differentiation Factor/Heregulin during Mitogenesis and is Constitutively Elevated in Growth Factor-independent Breast Carcinoma Cells with c-erbB-2 Gene Amplification[1];" *Cell Growth & Differentiation*; May 1996; pp. 551-561; vol. 7.

Richard M. Schultz, et al., "in Vitro and in Vivo Antitumor Activity of the Phosphatidylinositol-3-kinase Inhibitor, Wortmannin," *Anticancer Research* 15: 1135-1140 (1995).

\* cited by examiner

GENETIC ALTERATIONS ASSOCIATED WITH CANCER

CROSS REFERENCE TO RELATED APPLICATIONS

This is a continuation in part of application, U.S. Ser. No. 08/837,046, filed Apr. 5, 1997, now U.S. Pat. No. 6,110,673, which is a continuation in part of U.S. Ser. No. 08/783,729, filed Jan. 16, 1997, now U.S. Pat. No. 6,277,563 both of which are incorporated herein by reference.

STATEMENT AS TO RIGHTS TO INVENTIONS MADE UNDER FEDERALLY SPONSORED RESEARCH OR DEVELOPMENT

This invention was made with Government support under Grant No. CA09215, awarded by the National Institutes of Health. The Government has certain rights in this invention.

BACKGROUND OF THE INVENTION

Molecular genetic mechanisms responsible for the development and progression of many cancers remain largely unknown. Identification of sites of frequent and recurring allelic deletion or gain is a first step toward identifying some of the important genes involved in the malignant process. Previous studies in retinoblastoma (Friend, et al. *Nature,* 323: 643-6 (1986)) and other cancers (Cawthon, et al., *Cell,* 62:193-201 (1990); Baker, et al., *Science,* 244:217-21 (1989); Shuin, et al., *Cancer Res,* 54:2832-5 (1994)) have amply demonstrated that definition of regional chromosomal deletions occurring in the genomes of human tumors can serve as useful diagnostic markers for disease and are an important initial step towards identification of critical genes. Similarly, regions of common chromosomal gain have been associated with amplification of specific genes (Visakorpi, et al., *Nature Genetics,* 9:401-6 (1995)).

Comparative genomic hybridization (CGH) is a relatively new molecular technique used to screen DNA from tumors for regional chromosomal alterations (Kallioniemi, et al., *Science,* 258:818-21 (1992) and WO 93/18186). Unlike microsatellite or Southern analysis allelotyping studies, which typically sample far less than 0.1% of the total genome, a significant advantage of CGH is that all chromosome arms are scanned for losses and gains. Moreover, because CGH does not rely on naturally occurring polymorphisms, all regions are informative, whereas polymorphism-based techniques are limited by homozygous (uninformative) alleles among a fraction of tumors studied at every locus.

Increases in copy number in the long arm of chromosome 3, in particular 3q25-3qter, has been associated with cancer. Increases in copy number in this area have been seen not only in ovarian tumors (Iwabuchi et al., *Cancer Research* 55:6172-8180 (1995) and Arnold et al., *Genes Chromosomes Cancer* 16:46-54 (1996)) but also in brain tumors, head and neck cancer, lung cancer, ductal breast cancer, renal cell and other urinary tract cancers, and cervical cancer. Ried et al., *Genes Chromosomes Cancer* 15:234-245 (1996); Yeatman et al. *Clin Exp Metastasis* 14:246-252 (1996); Brzoska et al., *Cancer Res* 15:3055-3059 (1995); Ried et al., *Cancer Res* 54:1801-1806 (1994); Cher et al. *Cancer Research* 56:3091-3102 (1996); Heselmeyer et al., *Proc. Natl. Acad. Sci. USA* 93:479-484 (1996); Levin et al. *Genes Chromosomes Cancer* 13:175-185 (1995); and Speicher et al., *Cancer Res* 55:1010-3 (1995).

The identification of narrower regions of genetic alteration or genes associated with cancers such as ovarian cancer would be extremely useful in the early diagnosis or prognosis of these diseases. The present invention addresses these and other needs.

SUMMARY OF THE INVENTION

The present invention provides compositions and methods for detecting genetic alterations correlated with cancer. The invention can be used to detect alterations in a 2 MB region at 3q26.3 that are associated with a number of cancers. Examples include ovarian cancer, brain cancer, lung cancer, head and neck tumors, renal cell and other urinary tumors, cervical cancer, and ductal breast cancer. The invention is particularly useful for detecting alterations associated with ovarian cancer.

The methods comprise contacting a nucleic acid sample from a patient with a probe which binds selectively to a target nucleic acid sequence on 3q26.3 correlated with cancer. The target region is typically between markers D3S1275 or D3S1266 and D3S1548. In particular, the invention provides sequences from genes encoding the catalytic subunit of phosphatidylinositol kinase type 3 (PIK3CA) or the glucose transporter, GLUT2. The probes of the invention are contacted with the sample under conditions in which the probe binds selectively with the target nucleic acid sequence to form a hybridization complex. The formation of the hybridization complex is then detected. Typically, the number of regions of hybridization are counted. Abnormalities are detected as increases above normal in the regions of hybridization. In some embodiments, the methods of the invention further comprise detection of amplifications at 19q13.1-13.2. This region includes AKT2, a putative oncogene.

Alternatively, sample DNA from the patient can be fluorescently labeled and competitively hybridized against fluorescently labeled normal DNA to normal lymphocyte metaphases or to arrays of nucleic acid molecules which map to 3q26.3. Alterations in DNA copy number in the sample DNA are then detected as increases in sample DNA as compared to normal DNA at the 3q26.3 region.

DEFINITIONS

A "nucleic acid sample" as used herein refers to a sample comprising DNA in a form suitable for hybridization to a probes of the invention. The nucleic acid may be total genomic DNA, total mRNA, genomic DNA or mRNA from particular chromosomes, or selected sequences (e.g. particular promoters, genes, amplification or restriction fragments, cDNA, etc.) within particular cancer-associated amplifications. The nucleic acid sample may be extracted from particular cells or tissues. The tissue sample from which the nucleic acid sample is prepared is typically taken from a patient suspected of having the disease associated with the amplification being detected. The sample may be prepared such that individual nucleic acids remain substantially intact and typically comprises interphase nuclei prepared according to standard techniques. A "nucleic acid sample" as used herein may also refer to a substantially intact condensed chromosome (e.g. a metaphase chromosome). Such a condensed chromosome is suitable for use as a hybridization target in in situ hybridization techniques (e.g. FISH). The particular usage of the term "nucleic acid sample" (whether as extracted nucleic acid or intact metaphase chromosome) will be readily apparent to one of skill in the art from the context in which the term is used. For instance, the nucleic acid sample can be a tissue or cell sample prepared for standard in situ hybridization methods described below. The sample is prepared such that individual chromosomes remain substantially intact and typically comprises metaphase spreads or interphase nuclei prepared according to standard techniques.

The sample may also be isolated nucleic acids immobilized on a solid surface (e.g., nitrocellulose) for use in Southern or dot blot hybridizations and the like. In some embodiments, the probe may be a member of an array of nucleic acids as described, for instance, in WO 96/17958. In some cases, the nucleic acids may be amplified using standard techniques such as PCR, prior to the hybridization. The sample is typically taken from a patient suspected of having cancer associated with the abnormality being detected.

A "chromosome sample" as used herein refers to a tissue or cell sample prepared for standard in situ hybridization methods described below. The sample is prepared such that individual chromosomes remain substantially intact and typically comprises metaphase spreads or interphase nuclei prepared according to standard techniques.

"Nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

"Subsequence" refers to a sequence of nucleic acids that comprise a part of a longer sequence of nucleic acids.

A "probe" or a "nucleic acid probe", as used herein, is defined to be a collection of one or more nucleic acid fragments whose hybridization to a target can be detected. The probe is typically labeled as described below so that its binding to the target can be detected. In some embodiments, the sample comprising the target nucleic acid is labeled and the probe is not labeled. For instance, when the probes are prepared as an array of nucleic acids which selectively bind a number of desired target sequences.

The probe is produced from a source of nucleic acids from one or more particular (preselected) portions of the genome, for example one or more clones, an isolated whole chromosome or chromosome fragment, or a collection of polymerase chain reaction (PCR) amplification products. The probes of the present invention are produced from nucleic acids found in the regions of genetic alteration as described herein. The probe may be processed in some manner, for example, by blocking or removal of repetitive nucleic acids or enrichment with unique nucleic acids. Thus the word "probe" may be used herein to refer not only to the detectable nucleic acids, but to the detectable nucleic acids in the form in which they are applied to the target, for example, with the blocking nucleic acids, etc. The blocking nucleic acid may also be referred to separately. What "probe" refers to specifically is clear from the context in which the word is used.

"Hybridizing" refers the binding of two single stranded nucleic acids via complementary base pairing.

"Bind(s) substantially" or "binds specifically" or "binds selectively" or "hybridizing specifically to" refers to complementary hybridization between a probe and a target sequence and embraces minor mismatches that can be accommodated by reducing the stringency of the hybridization media to achieve the desired detection of the target nucleic acid sequence. These terms also refer to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Typically, stringent conditions will be those in which the salt concentration is at least about 0.02 Na ion concentration (or other salts) at pH 7.0 to 8.3 and the temperature is at least about 60° C. Stringent conditions may also be achieved with the addition of destabilizing agents such as formamide.

One of skill will recognize that the precise sequence of the particular probes described herein can be modified to a certain degree to produce probes that are "substantially identical" to the disclosed probes, but retain the ability to bind substantially to the target sequences. Such modifications are specifically covered by reference to the individual probes herein. The term "substantial identity" of nucleic acid sequences means that a nucleic acid comprises a sequence that has at least 90% sequence identity, more preferably at least 95%, compared to a reference sequence using the methods described below using standard parameters.

Two nucleic acid sequences are said to be "identical" if the sequence of nucleotides in the two sequences is the same when aligned for maximum correspondence as described below. The term "complementary to" is used herein to mean that the complementary sequence is identical to all or a portion of a reference nucleic acid sequence.

Sequence comparisons between two (or more) nucleic acids are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85: 2444 (1988), by computerized implementations of these algorithms.

"Percentage of sequence identity" is determined by comparing two optimally aligned sequences over a comparison window, wherein the portion of the nucleic acid sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Another indication that nucleotide sequences are substantially identical is if two molecules hybridize to the same sequence under stringent conditions. Stringent conditions are sequence dependent and will be different in different circumstances. Generally, stringent conditions are selected to be about 5° C. lower than the thermal melting point ($T_m$) for the specific sequence at a defined ionic strength and pH. The Tm is the temperature (under defined ionic strength and pH) at which 50% of the target sequence hybridizes to a perfectly matched probe. Typically, stringent conditions will be those as described above.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The phrase "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to a protein under such conditions may require an antibody that is selected for its specificity for a particular protein. For example, antibodies can be raised to the particular proteins disclosed here. Such antibodies will bind the proteins and not any other proteins present in a biological sample. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

BRIEF DESCRIPTION OF THE DRAWINGS

FIG. 2A shows maps of ovarian cancer cell lines CAOV433, OVCAR-3, CAOV-3, CAOV420, CAOV432, CAOV429, OCC1 and SKOV-3. FIG. 2B shows maps of primary ovarian tumors. FIG. 2C shows maps of melanoma cell lines 355 and 457 and two breast cancer cell lines ZR-75-03 and MCF-7.

FIG. 4A shows $^3$H-thymidine incorporation measured by a 18 hour pulse following initiation of culture. FIG. 4B shows MTT dye conversion measured 96 hours following initiation of culture. Similar results were obtained with cells cultured in serum-free media or in the presence of 10 ng/ml EGF.

DESCRIPTION OF THE PREFERRED EMBODIMENT

Figure 1:
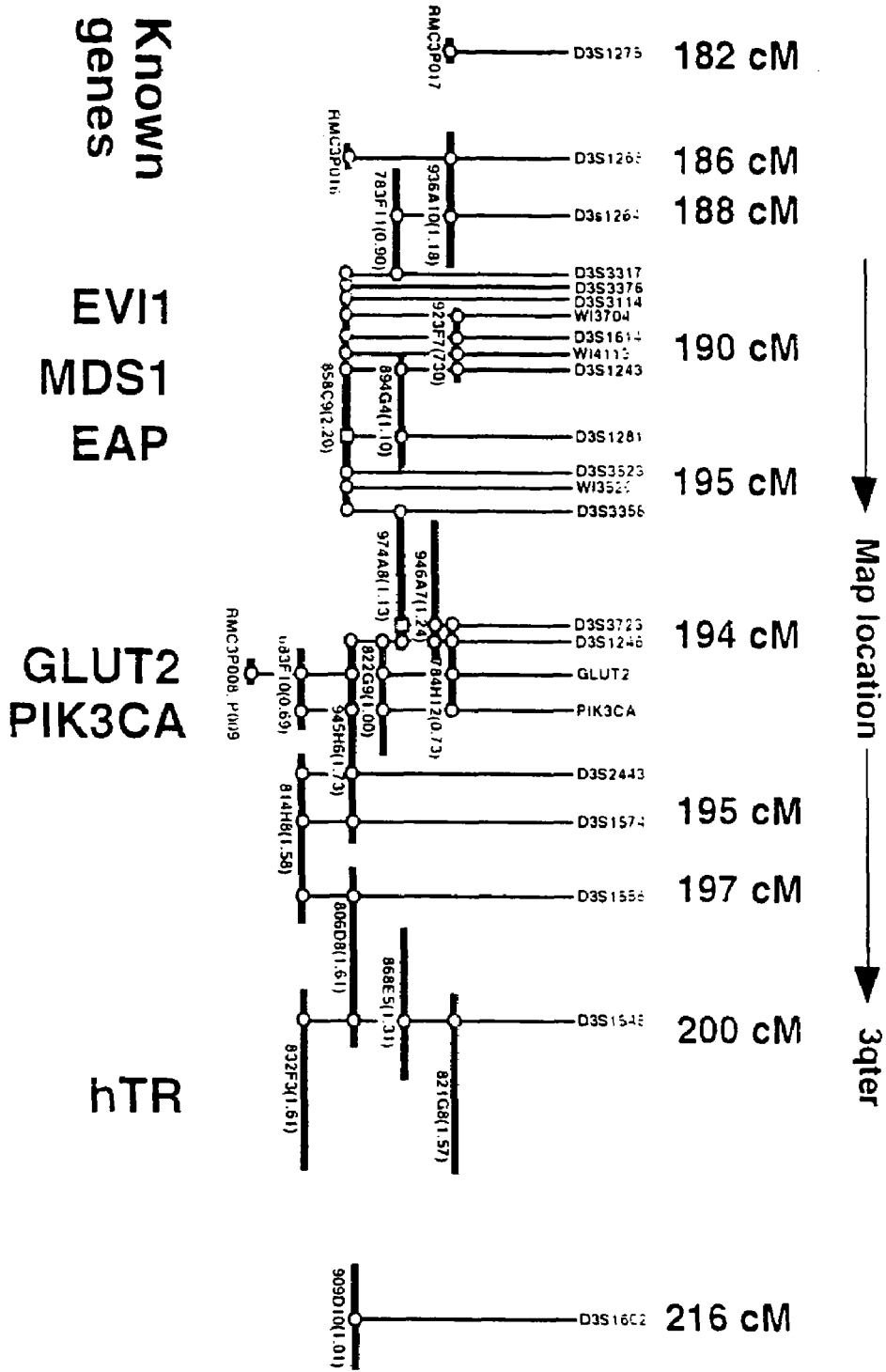
FIG. 1 is a schematic representation of a YAC/P1 physical map at chromosome 3q26 between D3S1275 and D3S1602. YACS are from the Genethon/CEPH mega YAC library and are illustrated as horizontal bars. Each YAC is listed by coordinate name. The size of each is listed in parentheses. P1 clones are listed by RMC number. Information about these probes is available through the Resource for Molecular Cytogenetics. STS evaluated in this study are listed above vertical lines showing their approximate locations. STSs contents of specific clones confirmed by PCR are listed as open circles. Predicted STS not confirmed by PCR are shown as open squares. Genes mapped within the YAC/P1 contig in this study or reported elsewhere (Dib et al. *Nature* 380:152-154 (1996); Gemmill et al. *Nature* 377:299-319 (1995); and Nucifora et al. *Blood* 86:1-14 (1995)) are shown below the clones to which they map.

Identification of Chromosomal Regions and Genes Associated with Cancer

The present invention is based on a comprehensive molecular cytogenetic analysis of the genomes of ovarian cancer cells using comparative genomic hybridization (CGH). CGH studies on epithelial ovarian cancer have revealed several regions that are present in increased or decreased copy number. More than 40% of these tumors show an increase in copy number on the long arm of chromosome 3, in particular in the region of 3q25-3qter (Iwabuchi et al., supra). This increase in copy number seems to be an early event for ovarian cancer. Increases in copy number in this region have also been observed in brain tumors, lung cancer, head and neck tumors, renal cell and other urinary tumors, cervical cancer, and ductal breast cancer.

Genomic regions that are found to be sites of increased DNA copy number in a large fraction of the cell lines and primary tumor cells are likely to include oncogenes that are present at increased copy number and hence overexpressed. Gene amplification is one method by which cells escape from normal controls of proliferation. The resulting overexpression or altered expression of these genes and their products is believed to play an important role in the development of a variety of human cancers (Weinberg, *Cancer* 61:1963-1968 (1988); Bishop, *Cell* 64: 235-248 (1991)).

The present invention is based in part on the discovery of specific cloned genomic DNA sequences showing increased copy number in a 2 MB region at 3q26.3 region. The region generally corresponds to region defined by markers D3S1275 or D3S1266 and D3S1548. Increased copy number was assessed using FISH and a number of P1, YAC, and cosmid clones known to map to this region. As shown below, probes associated with the region have shown an increase in copy number in ovarian cancer cell lines and ovarian tumor samples. The P1 was picked using PCR primers specific to the Glucose transporter gene, GLUT2. This gene is responsible for glucose signaling for beta cell insulin release. Its RNA product is found mostly in adult liver and pancreas, specifically in insulin-producing beta cells (Fukumoto et al., *Proc. Nat. Acad. Sci.* 85:5434-5438 (1988)). The sequence of cDNA from the gene is described in Fukumoto et al. This gene has been associated with is non-insulin-dependent diabetes mellitus (NIDDM). In NIDDM the highly conserved regions of this gene have been found mutated, resulting in abolished transport activity of the gene (Mueckler et al., *J. Biol. Chem.* 269:17765-17767 (1994)).

The 3q26 region also harbors the sequences for another gene, the catalytic subunit of phosphatidylinositol kinase type 3 (PI3K). The cloning of cDNA and genomic DNA encoding the catalytic subunit is described in Volinia et al. *Genomics* 24:472-477 (1994) and WO93/21328.

PIK3CA (also referred to as p110α), the 110 kD catalytic subunit of PI3-K binds to several isoforms of p85, a tyrosine kinase receptor adaptor protein, to form heterodimer proteins with PI3-kinase activity upon binding to activated tyrosine kinase receptors such as platelet derived growth factor (PDGF), insulin-like growth factor I (IGF-1), nerve growth factor (NGF), colony stimulating growth factor 1 (CSF-1) and epidermal growth factor (EGF). PI3-kinase activity also has been found to be increased in cells transformed with polyoma middle T, v-src, v-fnis and v-abl (Kapeller et al. *Bioessays* 16:565-576 (1994)). The PI3-kinase heterodimer is postulated to bind to phosphorylated transmembrane tyrosine kinase receptor dimers and associated proteins (e.g. ras-GAP, PLCg) through SH2 domains in the p85 adaptor subunit after which the p110 catalytic subunit, PIK3CA, phosphorylates phosphoinositides and possibly serine/threonine proteins as part of a signaling response. The mechanism of signal transduction for PI3-kinase is not completely understood. However, two protein kinases, the serine-threonine kinase, Akt (also known as protein kinase B and Rac) and the p70 ribosomal protein S6 kinase (p70S6K) have been placed downstream of PI3-kinase (see, Burgening and Coffer, Nature 376: 599-602 (1995); Franke et al., Cell 81:727-736 (1995)). Akt activity appears to be regulated by binding of phosphatidylinositol-3,4-biphosphate (Ptdins-3,4-P2) to a pleckstrin homology domain (Franke et al, *Cell* 88:435-437 (1997)).

In addition, PI3K is required to maintain basal and insulin stimulated glucose and amino acid transport (Tsakiridis et al., *Endocrinology* 136:4315-4322 (1995)). It is therefore likely that an increased expression in PI3K levels could also upregulate the nearby GLUT2 gene. As explained below, compounds that inhibit expression of these genes or inhibit activity of the encoded protein have therapeutic potential in cancers, such as ovarian cancer.

A number of high molecular weight kinases have been cloned that have sequence similarities to PIK3CA. These kinases have a range of cellular functions such as meiotic and V(D)j recombination, chromosome maintenance and repair, cell cycle progression, and cell cycle checkpoints, and with dysfunctions resulting in medical disorders ranging from a loss of immunological function to cancer. Therefore, increases in copy number in the PIK3CA in ovarian tumor samples may have implications in the level of tumor aggressiveness or patient prognosis, and the analysis of this gene at the tumor level could improve early diagnosis, and assist in better patient therapy and survival for this disease.

In some embodiments of the invention, probes specific to 19q13.1-13.2 can be used in the methods, as well. Amplification of this region has been correlated with ovarian cancer using FISH and molecular studies (see, e.g., Thompson et al. *Cancer Genet Cytogenet* 87: 55-62 (1996)). The AKT2 gene, discussed above, is located in this region. AKT2 encodes a member of a subfamily of protein-serine/threonine kinases and is thought to be a human homologue of an oncogene isolated from the retrovirus, AKT8. Staal, *Proc Natl Acad Sci USA* 84:5034-7 (1987). A cDNA encoding the protein is described by Cheng et al. *Proc Natl Acad Sci USA* 89: 9267-71 (1992). Amplification of 19q13. 1-13.2 region and overexpression of the AKT2 gene have been identified in ovarian and pancreatic cancer (see, e.g., Bellacosa et al., supra, Thompson et al. supra, and Miwa et al. *Biochem Biophys Res Commun* 225:968-74 (1996)). Inhibition of AKT2 expression and tumorigenicity has been demonstrated using antisense RNA. Cheng et al. *Proc Natl Acad Sci USA* 93:3636-41 (1996).

AKT activity appears to be regulated by binding of phosphatidylinositol-3,4-biphosphate (Ptdins-3,4-P$_2$) to a pleckstrin homology domain. The activation of AKT has been associated with increased cell survival through a reduction in apoptosis. Without wishing to be bound by theory, it is believed that amplification of PIK3CA in ovarian cancer contributes to cancer progression and/or initiation by reducing apoptotic death and increasing cell proliferation rate. The possible decrease in apoptosis is relevant since apoptosis likely plays an important role removal of epithelial cells that become detached from the stroma during ovulation. Reduced apoptosis in these cells might lead to malignancy since severed studies now suggest that disruption of the stroma (e.g. by overexpression of metalloproteinases) causes cancer in murine mammary cells.

In the present invention it has been found that both the PIK3CA and AKT2 genes are amplified in cancers, such as ovarian cancer. Thus, detection of amplification and/or overexpression of these genes is useful in the early diagnosis of cancers.

In addition, in some embodiments, the expression of other genes associated with cancer (e.g., tumor suppressor genes or oncogenes) can be monitored in the present invention. For instance, expression of wild-type p53 can be monitored according to known techniques. Mutation or loss of the p53 gene is the most common genetic alteration in human cancers (Bartek et al. (1991) *Oncogene*, 6: 1699-1703, Hollstein et al. (1991) *Science*, 253: 49-53).

Preparation of Probes of the Invention

A number of methods can be used to identify probes which hybridize specifically to the 3q26 region other than those exemplified here. For instance, probes can be generated by the random selection of clones from a chromosome specific library, and then mapped to each chromosome or region by digital imaging microscopy. This procedure is described in U.S. Pat. No. 5,472,842. Briefly, a genomic or chromosome specific DNA is digested with restriction enzymes or mechanically sheared to give DNA sequences of at least about 20 kb and more preferably about 40 kb to 300 kb. Techniques of partial sequence digestion are well known in the art. See, for example Perbal, *A Practical Guide to Molecular Cloning* 2nd Ed., Wiley N.Y. (1988). The resulting sequences are ligated with a vector and introduced into the appropriate host. Exemplary vectors suitable for this purpose include cosmids, yeast artificial chromosomes (YACs), bacterial artificial chromosomes (BACs) and P1 phage. Typically, cosmid libraries are prepared. Various libraries spanning entire chromosomes are also available commercially from for instance Genome Systems.

Once a probe library is constructed, a subset of the probes is physically mapped on the selected chromosome. FISH and digital image analysis can be used to localize clones along the desired chromosome. Briefly, the clones are mapped by FISH to metaphase spreads from normal cells using e.g., FITC as the fluorophore. The chromosomes may be counterstained by a stain which stains DNA irrespective of base composition (e.g., propidium iodide), to define the outlining of the chromosome. The stained metaphases are imaged in a fluorescence microscope with a polychromatic beam-splitter to avoid color-dependent image shifts. The different color images are acquired with a CCD camera and the digitized images are stored in a computer. A computer program is then used to calculate the chromosome axis, project the two (for single copy sequences) FITC signals perpendicularly onto this axis, and calculate the average fractional length from a defined position, typically the p-telomere. This approach is described, for instance, in U.S. Pat. No. 5,472,842.

Sequence information of the genes identified here permits the design of highly specific hybridization probes or amplification primers suitable for detection of target sequences from these genes. As noted above, the complete sequence of these genes is known. Means for detecting specific DNA sequences within genes are well known to those of skill in the art. For instance, oligonucleotide probes chosen to be complementary to a selected subsequence within the gene can be used. Alternatively, sequences or subsequences may be amplified by a variety of DNA amplification techniques (for example via polymerase chain reaction, ligase chain reaction, transcription amplification, etc.) prior to detection using a probe. Amplification of DNA increases sensitivity of the assay by providing more copies of possible target subsequences. In addition, by using labeled primers in the amplification process, the DNA sequences may be labeled as they are amplified.

Labeling Probes

Methods of labeling nucleic acids are well known to those of skill in the art. Preferred labels are those that are suitable for use in in situ hybridization. The nucleic acid probes may be detectably labeled prior to the hybridization reaction. Alternatively, a detectable label which binds to the hybridization product may be used. Such detectable labels include any material having a detectable physical or chemical property and have been well-developed in the field of immunoassays.

As used herein, a "label" is any composition detectable by spectroscopic, photochemical, biochemical, immunochemical, or chemical means. Useful labels in the present invention include radioactive labels (e.g. $^{32}P$, $^{125}I$, $^{14}C$, $^{3}H$, and $^{35}S$), fluorescent dyes (e.g. fluorescein, rhodamine, Texas Red, etc.), electron-dense reagents (e.g. gold), enzymes (as commonly used in an ELISA), colorimetric labels (e.g. colloidal gold), magnetic labels (e.g. DynabeadS™), and the like. Examples of labels which are not directly detected but are detected through the use of directly detectable label include biotin and dioxigenin as well as haptens and proteins for which labeled antisera or monoclonal antibodies are available.

The particular label used is not critical to the present invention, so long as it does not interfere with the in situ hybridization of the probe. However, probes directly labeled with fluorescent molecules (e.g. fluorescein-12-dUTP, Texas Red-5-dUTP, etc.) are preferred for chromosome hybridization.

A direct labeled probe, as used herein, is a probe to which a detectable label is attached. Because the detectable label is already attached to the probe, no subsequent steps are required to associate the probe with the detectable label. In contrast, an indirect labeled probe is one which bears a moiety to which a detectable label is subsequently bound, typically after the probe is hybridized with the target nucleic acid.

In addition the label must be detectible in as low copy number as possible thereby maximizing the sensitivity of the assay and yet be detectible above any background signal. Finally, a label must be chosen that provides a highly localized signal thereby providing a high degree of spatial resolution when physically mapping the stain against the chromosome. Particularly preferred fluorescent labels include fluorescein-12-dUTP and Texas Red-5-dUTP.

The labels may be coupled to the probes in a variety of means known to those of skill in the art. In some embodiments the nucleic acid probes are labeled using nick translation or random primer extension (Rigby, et al. *J. Mol. Biol.*, 113: 237 (1977) or Sambrook et al., *Molecular Cloning—A Laboratory Manual*, Cold Spring Harbor Laboratory, Cold Spring Harbor, N.Y., (1989)). Particularly preferred methods for labeling probes are described in U.S. Pat. No. 5,491,224. These methods involve direct labeling the probes by chemical modification of cytosine residues.

Use of Nucleic Acids of the Invention to Detect Chromosomal Alterations

Using the results provided here, one of skill can prepare nucleic acid probes specific to the 3q26 region of genetic alteration that is associated with ovarian and other cancer. In particular, nucleic acid sequences from the GLUT2 gene or the PIK3CA gene can be used to detect copy number increase of these genes. The probes can be used in a variety of nucleic acid hybridization assays to detect the presence (in particular increased copy number) of the target gene. Thus, the probes are useful, for example, in the early diagnosis or prognosis of cancer. As noted above, the probes are particularly useful for detecting alteration associated with ovarian cancer. The regions can also be used for a large number of other cancers as described above.

The genetic alterations are detected through the hybridization of a probe of this invention to a nucleic acid sample in which it is desired to screen for the alteration. Suitable hybridization formats are well known to those of skill in the art and include, but are not limited to, variations of Southern Blots, northern blots, CGH, in situ hybridization and quantitative amplification methods such as quantitative PCR (see, e.g. Sambrook et al., Kallioniemi et al., *Proc. Natl. Acad Sci USA*, 89: 5321-5325 (1992), and *PCR Protocols, A Guide to Methods and Applications*, Innis et al., Academic Press, Inc. N.Y., (1990)).

The sample used in the methods will, of course, depend upon the particular method used to detect the target. For instance, the nucleic acid sample can be a tissue or cell sample prepared for standard in situ hybridization methods. The sample or probes may also be isolated nucleic acids immobilized on a solid surface (e.g., nitrocellulose) for use in Southern or dot blot hybridizations and the like. In some embodiments, the probes of the invention may comprise an array of nucleic acids as described, for instance, in WO 96/17958).

In a preferred embodiment, the regions disclosed here are identified using in situ hybridization. Generally, in situ hybridization comprises the following major steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments. The reagent used in each of these steps and their conditions for use vary depending on the particular application.

In some applications it is necessary to block the hybridization capacity of repetitive sequences. In this case, human genomic DNA or Cot1 DNA is used as an agent to block such hybridization. The preferred size range is from about 200 bp to about 1000 bases, more preferably between about 400 to about 800 bp for double stranded, nick translated nucleic acids.

Hybridization protocols for the particular applications disclosed here are described in Pinkel et al. *Proc. Natl. Acad. Sci. USA*, 85: 9138-9142 (1988) and in EPO Pub. No. 430,402. Suitable hybridization protocols can also be found in *Methods in Molecular Biology Vol. 33: In Situ Hybridization Pro-*

*tocols*, K. H. A. Choo, ed., Humana Press, Totowa, N.J., (1994). In a particularly preferred embodiment, the hybridization protocol of Kallioniemi et al., *Proc. Natl. Acad Sci USA*, 89: 5321-5325 (1992) is used.

Typically, it is desirable to use dual color FISH, in which two probes are utilized, each labeled by a different fluorescent dye. A test probe that hybridizes to the region of interest is labeled with one dye, and a control probe that hybridizes to a different region is labeled with a second dye. A nucleic acid that hybridizes to a stable portion of the chromosome of interest, such as the centromere region, is often most useful as the control probe. In this way, differences between efficiency of hybridization from sample to sample can be accounted for.

The FISH methods for detecting chromosomal abnormalities can be performed on nanogram quantities of the subject nucleic acids. Paraffin embedded tumor sections can be used, as can fresh or frozen material. Because FISH can be applied to the limited material, touch preparations prepared from uncultured primary tumors can also be used (see, e.g., Kallioniemi, A. et al., *Cytogenet. Cell Genet.* 60: 190-193 (1992)). For instance, small biopsy tissue samples from tumors can be used for touch preparations (see, e.g., Kallioniemi, A. et al., *Cytogenet. Cell Genet.* 60: 190-193 (1992)). Small numbers of cells obtained from aspiration biopsy or cells in bodily fluids (e.g., blood, urine, sputum and the like) can also be analyzed.

In various blot formats (e.g., dot blots, Southern blots, and Northern blots) nucleic acids (e.g., genomic DNA, cDNA or RNA) are hybridized to a probe specific for the target region. Either the probe or the target can be immobilized on the solid surface. Comparison of the intensity of the hybridization signal from the probe for the target region with the signal from a probe directed to a control (non amplified or deleted) such as centromeric DNA, provides an estimate of the relative copy number of the target nucleic acid. Procedures for carrying out Southern hybridizations are well known to those of skill in the art. see, e.g., Sambrook et al., supra.

Other hybridization formats use arrays of probes or targets to which nucleic acid samples are hybridized as described, for instance, in WO 96/17958. Techniques capable of producing high density arrays can also be used for this purpose (see, e.g., Fodor et al. *Science* 767-773 (1991) and U.S. Pat. No. 5,143,854). As used herein, a "nucleic acid array" is a plurality of target elements, each comprising one or more target nucleic acid molecules immobilized on a solid surface to which probe nucleic acids are hybridized. Target nucleic acids of a target element typically have their origin in the 3q26 region disclosed here. The target nucleic acids of a target element may, for example, contain sequence from specific genes or clones disclosed here. Target elements of various dimensions can be used in the arrays of the invention. Generally, smaller, target elements are preferred. Typically, a target element will be less than about 1 cm in diameter. Generally element sizes are from 1 μm to about 3 mm, preferably between about 5 μm and about 1 mm.

The target elements of the arrays may be arranged on the solid surface at different densities. The target element densities will depend upon a number of factors, such as the nature of the label, the solid support, and the like. One of skill will recognize that each target element may comprise a mixture of target nucleic acids of different lengths and sequences. Thus, for example, a target element may contain more than one copy of a cloned piece of DNA, and each copy may be broken into fragments of different lengths. The length and complexity of the target sequences of the invention is not critical to the invention. One of skill can adjust these factors to provide optimum hybridization and signal production for a given hybridization procedure, and to provide the required resolution among different genes or genomic locations. Typically, the target sequences will have a complexity less than about 1 Mb, sometimes 10 kb and about 500 kb, and usually from about 50 kb to about 150 kb.

Detection of Proteins of the Invention

The gene products described here (GLUT2 and PIK3CA) as well as gene products (e.g., AKT2) whose expression is effected by GLUT2 and PIK3CA can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In a preferred embodiment, the proteins are detected using an immunoassay. As used herein, an immunoassay is an assay that utilizes an antibody to specifically bind to the analyte (e.g., GLUT2, PIK3CA or AKT2 proteins). The immunoassay is thus characterized by detection of specific binding of the protein to an antibody raised against it as opposed to the use of other physical or chemical properties to isolate, target, and quantify the analyte (see, e.g., U.S. Pat. Nos. 4,366,241; 4,376,110; 4,517,288; and 4,837,168). For a review of the general immunoassays, see also *Methods in Cell Biology Volume 37: Antibodies in Cell Biology*, Asai, ed. Academic Press, Inc. New York (1993); *Basic and Clinical Immunology* 7th Edition, Stites & Terr, eds. (1991).

The proteins are preferably quantified in a biological sample derived from a mammal, more preferably from a human patient. As used herein, a biological sample is a sample of biological tissue or fluid that contains a protein concentration that may be correlated with amplification of the 3q regions disclosed here. Particularly preferred biological samples include, but are not limited to biological fluids such as whole blood, serum, or urine, or tissue samples including, but not limited to tissue biopsy (e.g., needle biopsy) samples.

The antibody (e.g., anti-GLUT2, anti-PIK3CA or anti-AKT2) may be produced by any of a number of means well known to those of skill in the art (see, e.g. *Methods in Cell Biology Volume 37: Antibodies in Cell Biology*, Asai, ed. Academic Press, Inc. New York (1993); and *Basic and Clinical Immunology* 7th Edition, Stites & Terr, eds. (1991)). The antibody may be a whole antibody or an antibody fragment. It may be polyclonal or monoclonal, and it may be produced by challenging an organism (e.g. mouse, rat, rabbit, etc.) with one of these proteins or an epitope derived therefrom. Alternatively, the antibody may be produced de novo using recombinant DNA methodology. The antibody can also be selected from a phage display library screened against the protein (see, e.g. Vaughan et al. (1996) *Nature Biotechnology*, 14: 309-314 and references therein).

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled protein or a labeled antibody. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species. See, generally Kronval, et al., *J. Immunol.*, 111: 1401-1406 (1973), and Akerstrom, et al., *J. Immunol.*, 135:2589-2542 (1985).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

Immunoassays for detecting the proteins may be either competitive or noncompetitive. Noncompetitive immunoassays are assays in which the amount of captured analyte (e.g., PIK3CA) is directly measured. In one preferred "sandwich" assay, for example, the capture agent (anti-PIK3CA antibodies) can be bound directly to a solid substrate where they are immobilized. These immobilized antibodies then capture protein present in the test sample. The PIK3CA protein thus immobilized is then bound by a labeling agent, such as a second PIK3CA antibody bearing a label. Alternatively, the second PIK3CA antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

In competitive assays, the amount of analyte (e.g., PIK3CA) present in the sample is measured indirectly by measuring the amount of an added (exogenous) analyte displaced (or competed away) from a capture agent (e.g., anti-PIK3CA antibody) by the analyte present in the sample. In one competitive assay, a known amount of, for instance, PIK3CA, is added to the sample and the sample is then contacted with a capture agent such as an antibody that specifically binds PIK3CA protein. The amount of PIK3CA protein bound to the antibody is inversely proportional to the concentration of PIK3CA protein present in the sample.

In another embodiment, the antibody (e.g., anti-PIK3CA) is immobilized on a solid substrate. The amount of PIK3CA protein bound to the antibody may be determined either by measuring the amount of PIK3CA present in an protein/antibody complex, or alternatively by measuring the amount of remaining uncomplexed PIK3CA protein. The amount of protein may be detected by providing a labeled PIK3CA protein.

A hapten inhibition assay is another preferred competitive assay. In this assay a known analyte (e.g., PIK3CA protein) is immobilized on a solid substrate. A known amount of anti-PIK3CA antibody is added to the sample, and the sample is then contacted with the immobilized PIK3CA protein. In this case, the amount of anti-PIK3CA antibody bound to the immobilized protein is inversely proportional to the amount of PIK3CA present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

In other embodiments, Western blot (immunoblot) analysis is used to detect and/or quantify the presence of the proteins in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the desired protein. Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34-41).

The particular label or detectable group used in an immunoassay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g. polystyrene, polypropylene, latex, etc.) beads.

Kits of the Invention.

This invention also provides diagnostic kits for the detection of chromosomal abnormalities at the regions disclosed here. For instance, the kits may include one or more nucleic acid probes to the regions described herein. The kits can additionally include blocking probes, instructional materials describing how to use the kit contents in detecting the alterations. The kits may also include one or more of the following: various labels or labeling agents to facilitate the detection of the probes, reagents for the hybridization including buffers, a metaphase spread, bovine serum albumin (BSA) and other blocking agents, sampling devices including fine needles, swabs, aspirators and the like, positive and negative hybridization controls and so forth.

Alternatively, the kits can be used for detection of the gene products disclosed here. In these embodiments, the kits will contain reagents for detecting proteins (e.g., GLUT2, PIK3CA or AKT2) or antibodies against them in serum or other biological fluids. Such a kit includes antibodies which specifically recognize the target proteins and a labeling system, including enzyme substrates and the like, suitable for detecting the immune complexes formed by the target antigens and antibodies. The kits also include appropriate washing solutions, dilution buffers and the like for preparation and analysis of biological samples.

Therapeutic Uses of Genes and their Gene Products

The genes identified here (e.g., PIK3CA and GLUT2) and their polypeptide products can be used to modulate the activity of the gene products of endogenous genes. Alternatively, the activity of gene products in biochemical pathways controlled by PIK3CA or GLUT2 expression (e.g., AKT2) can be modulated. By modulating activity of the gene products, pathological conditions associated with their overexpression or lack of expression can be treated. Any of a number of techniques well known to those of skill in the art can be used for this purpose.

The genes of the invention are particularly used for the treatment of various cancers such as cancers of the ovaries. Other diseases may also be treated with the sequences of the invention.

The polypeptides encoded by the genes can be used as immunogens to raise antibodies either polyclonal or monoclonal. The antibodies can be used to detect the polypeptides as therapeutic agents to inhibit the polypeptides, or as targeting moieties in immunotoxins. The production of monoclonal antibodies against a desired antigen is well known to those of skill in the art and is not reviewed in detail here.

The PIK3CA or GLUT2 genes are particularly useful for gene therapy techniques well known to those skilled in the art. Gene therapy as used herein refers to the multitude of techniques by which gene expression may be altered in cells. Such methods include, for instance, introduction of DNA encoding ribozymes or antisense nucleic acids to inhibit expression as well as introduction of functional wild-type genes to replace mutant genes. A number of suitable viral vectors are known. Such vectors include retroviral vectors (see Miller, *Curr. Top. Microbiol. Immunol.* 158: 1-24 (1992); Salmons and Gunzburg, *Human Gene Therapy* 4: 129-141 (1993); Miller et al., *Methods in Enzymology* 217: 581-599, (1994)) and adeno-associated vectors (reviewed in Carter, *Curr. Opinion Biotech.* 3: 533-539 (1992); Muzcyzka, *Curr. Top. Microbiol. Immunol.* 158: 97-129 (1992)). Other viral vectors that may be used within the methods include adenoviral vectors, herpes viral vectors and Sindbis viral vectors, as generally described in, e.g., Jolly, *Cancer Gene Therapy* 1:51-64 (1994); Latchman, *Molec. Biotechnol.* 2:179-195 (1994); and Johanning et al., *Nucl. Acids Res.* 23:1495-1501 (1995).

Delivery of nucleic acids linked to a heterologous promoter-enhancer element via liposomes is also known (see, e.g., Brigham, et al. (1989) *Am. J. Med. Sci.,* 298:278-281; Nabel, et al. (1990) *Science,* 249:1285-1288; Hazinski, et al. (1991) *Am. J. Resp. Cell Molec. Biol.,* 4:206-209; and Wang and Huang (1987) *Proc. Natl. Acad. Sci.* (*USA*), 84:7851-7855); coupled to ligand-specific, cation-based transport systems (Wu and Wu (1988) *J. Biol. Chem.,* 263:14621-14624). Naked DNA expression vectors have also been described (Nabel et al. (1990), supra); Wolff et al. (1990) *Science,* 247:1465-1468).

The nucleic acids and encoded polypeptides of the invention can be used directly to inhibit the endogenous genes or their gene products. For instance, inhibitory nucleic acids may be used to specifically bind to a complementary nucleic acid sequence. By binding to the appropriate target sequence, an RNA-RNA, a DNA-DNA, or RNA-DNA duplex is formed. These nucleic acids are often termed "antisense" because they are usually complementary to the sense or coding strand of the gene, although approaches for use of "sense" nucleic acids have also been developed. The term "inhibitory nucleic acids" as used herein, refers to both "sense" and "antisense" nucleic acids. Inhibitory nucleic acid methods encompass a number of different approaches to altering expression of specific genes that operate by different mechanisms.

In brief, inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids (ribozymes). These different types of inhibitory nucleic acid technology are described, for instance, in Helene, C. and Toulme, J. (1990) *Biochim. Biophys. Acta.,* 1049:99-125. Inhibitory nucleic acid complementary to regions of c-myc mRNA has been shown to inhibit c-myc protein expression in a human promyelocytic leukemia cell line, HL60, which overexpresses the c-myc proto-oncogene. See Wickstrom E. L., et al., (1988) *PROC. ACAD. SCI. USA* (*USA*), 85:1028-1032 and Harel-Bellan, A., et al., (1988) *Exp. Med.,* 168:2309-2318.

The encoded polypeptides of the invention can also be used to design molecules (peptidic or nonpeptidic) that inhibit the endogenous proteins by, for instance, inhibiting interaction between the protein and a second molecule specifically recognized by the protein. Methods for designing such molecules are well known to those skilled in the art.

For instance, polypeptides can be designed which have sequence identity with the encoded proteins or may comprise modifications (conservative or non-conservative) of the sequences. The modifications can be selected, for example, to alter their in vivo stability. For instance, inclusion of one or more D-amino acids in the peptide typically increases stability, particularly if the D-amino acid residues are substituted at one or both termini of the peptide sequence.

The polypeptides can also be modified by linkage to other molecules. For example, different N- or C-terminal groups may be introduced to alter the molecule's physical and/or chemical properties. Such alterations may be utilized to affect, for example, adhesion, stability, bio-availability, localization or detection of the molecules.

Alternatively, other non-peptidic compounds which inhibit the activity of the gene products described here can be used to treat cancer. For instance, compounds which inhibit PIK3CA activity (e.g., Y294002, Wortmannin, Rapamycin) can be used therapeutically. A number of glucose transport inhibitors are available. Exemplary glucose transport inhibitors include cytochalasin B and ethanol (see, e.g., Colville et al. *Biochemical Journal* 290:701-706 (1993) and Nagamatsu et al., *Bioch. Molec. Biol. Int.* 37:675-680 (1995)).

Pharmaceutical compositions containing the inhibitory compounds of the invention (e.g., polypeptides, nucleic acids, non-peptidic inhibitors of enzyme activity) are suitable for use in a variety of drug delivery systems. Suitable formulations for use in the present invention are found in *Remington's Pharmaceutical Sciences*, Mack Publishing Company, Philadelphia, Pa., 17th ed. (1985).

The subject compounds, by themselves or as conjugates, may be prepared as formulations in pharmaceutically acceptable media, for example saline, PBS, and glucose, generally at a therapeutically effective dose, the concentrations of which will be determined empirically in accordance with conventional procedures for the particular purpose. The additives may include bactericidal agents, stabilizers, buffers, or the like.

In order to enhance serum half-life, polypeptides may be encapsulated, introduced into the lumen of liposomes, prepared as a colloid, or other conventional technique may be employed which provides an extended serum half-life of the peptides. A variety of methods are available for preparing liposomes, as described in, e.g., Szoka et al., *Ann. Rev. Biophys. Bioeng.* 9:467 (1980), U.S. Pat. Nos. 4,235,871, 4,501,728 and 4,837,028, all of which are incorporated herein by reference.

The amount of inhibitory compound administered to the patient will vary depending upon what is being administered, the purpose of the administration, such as the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient.

The pharmaceutical compositions are intended for parenteral, topical, oral or local administration, such as by aerosol or transdermally, for prophylactic and/or therapeutic treatment. Commonly, the pharmaceutical compositions are administered parenterally, e.g., intravenously or intraperitonealy.

Two or more inhibitory compounds of the invention may be combined to form a "cocktail" under certain circumstances for increased efficacy. The compounds of the invention may also be used in conjunction with other pharmaceutically active agents.

EXAMPLES

Example 1

This example describes the identification of genes in a 2 MB region at 3q26.3 region. Increased copy number of this region is correlated with ovarian cancer.

CGH studies have identified DNA copy number abnormalities at 3q25-26 associated with ovarian tumors (Iwabuchi et al., *Cancer Research* 55:6172-8180 (1995)). To physically map the 3q26 region, a number of yeast artificial chromosome (YAC), P1, and cosmid clones that were known to genetically map to the region were physically mapped to the 3q region. Several yeast artificial chromosome (YAC) and P1 clones known to genetically map to this region were physically mapped using FISH and fractional length analysis. Clone positions were reconfirmed by PCR using STSs specific to the region. Clones were then picked according to their physical map position and hybridized onto interphase cells of ovarian cancer, breast cancer, and melanoma cell lines, as well as nuclei of paraffin-embedded ovarian tumors. One of the P1 clones and its 5 associated YAC clones have shown increases in copy number in 8 ovarian cancer cell lines and 6 primary ovarian tumor samples, small increases in copy number in the breast cancer lines, and no increases in copy number in the melanoma lines. Based on these results, the region of increased copy number was narrowed to a 2 MB region at 3q26.3.

Materials and Methods

Probes. Yeast artificial chromosome (YAC) clones were obtained from Genethon/CEPH of France. YAC clones were chosen based on their genetic map along 3q24-3qter. Each YAC was grown and checked for chimerism by FISH. P1 clones were obtained by screening a human genomic P1 library (DuPont, Boston, Mass.) using PCR with primers specific to chromosome 3. Those P1 clones mapping to 3q25-3qter were used for further study. A P1 clone mapping to the 3p region was used throughout the experiments as a reference marker.

Nonchimeric YAC clones as well as all the P1 clones were mapped onto chromosome 3 by digital image analysis of their physical distance from the terminus of the p arm (Flpter analysis) generally as described in Mascio, et al. *Cytometry* 19:51-9 (1995) and Sakamoto et al, *Cytometry* 19:60-9 (1995)).

All probes were labeled for hybridization by random priming (BioPrime kit, BRL). The 3q region probes were labeled with digoxigenin-11-dUTP (Boehringer-Mannheim) and detected using Fluorescein-antidigoxigenin. The reference P1 probe on 3p was directly labeled with Texas-Red dUTP (NEN DuPont).

Normal human metaphase spreads, cell lines, and paraffin-embedded tumor samples. Normal human metaphase spreads were prepared as previously described (Kallioniemi et al., supra). Slides were denatured in 70% formamide/2×SSC at 72 degrees for 3 to 10 minutes (depending on the slide batch) and then serially dried in 70%, 85%, and 100% ethanol.

Ovarian cancer cell lines SKOV3, CAOV3, CAOV433, CAOV420, CAOV432, CAOV429, OCC1 and OVCAR3 and breast cancer cell lines MCF-7 and MDA-MDB-453 were obtained from ATCC. Melanoma cell lines 355 and 457 were kindly provided by Dr. Taetle (University of Arizona). All cells were resuspended in 2 ml of 0.075M KCl hypotonic solution, incubated at 37 degrees for 20 minutes, fixed, and dropped onto slides.

Paraffin-embedded epithelial ovarian tumor samples were provided by Dr. Teresa Yang-Feng (Yale University). All samples were checked to contain >60% tumor cells. These samples were deparaffinized, using xylene, washed with ethanol, then with water, digested with pepsin, and cytospun onto slides in order to concentrate the cell population.

FISH, physical mapping, and slide scorings. Cell line and normal metaphase slides were denatured in 70% formamide/2×SSC for 5 minutes at 72 degrees, followed by drying through 70%, 85%, and 100% ethanol. Paraffin-embedded tumor materials were fixed for 10 minutes in methanol-acefic acid (3:1) prior to denaturation in 70% formamide/2×SSC for 10 minutes at 80 degrees, then digested with 5 ug/Ml proteinase K for 10 minutes at 37 degrees, followed by drying through 70%, 85%, and 100% ethanol for 2 minutes each.

40 ng of each probe was placed on each slide along with 5 ug Cot1 DNA (to suppress repetitive sequences) in a total of 10 ul of 50% formamide/2×SSC/10% dextran sulfate, and slides were coverslipped and sealed. After an overnight incubation at 37 degrees, slides were washed to remove unbound probes, stained immunochemically with fluoresceinantidigoxigenin, counterstained with 0.2 uM 4,6-diamino-2-phenylindole in antifade solution for chromosome identification, and visualized under fluorescent microscope. For physical mapping, multicolor images of metaphase chromosomes and their associated probes were acquired using the QUIPS (quantitative image processing system). Analysis of the hybridization signals is completely automated, and carried out using the Xquips software (Mascio, et al. *Cytometry* 19:51-9 (1995) and Sakamoto et al, *Cytometry* 19:60-9 (1995)). Briefly, analysis consisted of chromosome segmentation, medial axis calculation, hybridization domain segmentation, center of mass calculation, and contrast enhancement. Fractional location of a domain was determined from the end of the short arm to the valid hybridization signal (Flpter analysis). On average, 20 Flpter measurements were made for each probe, and probe location on a chromosome was reported as the mean+/− one standard error of the mean of the measurements. Probe order was determined from the mean Flpter values.

For interphase cells, simultaneous Texas Red and Fluorescein signals were visualized using a double bandpass filter on the X63 objective of a Zeiss Axioscope camera. At least 100 cells were counted for each probe set.

Results

Physical mapping. FIG. 1 shows the genomic organization of the clones used in this study. In addition, the order of the clones for the region of interest was also checked by PCR using several STSs known to map to this region and confirmed by comparing these results to the recently published YAC maps in the Genome Directory Naylor et al., *Cytogenet. Cell Genet.* 72: 255-70 (1995) and the Whitehead institute's integrated map Dib et al., *Nature* 380:152-4 (1996).

Figure 2A:
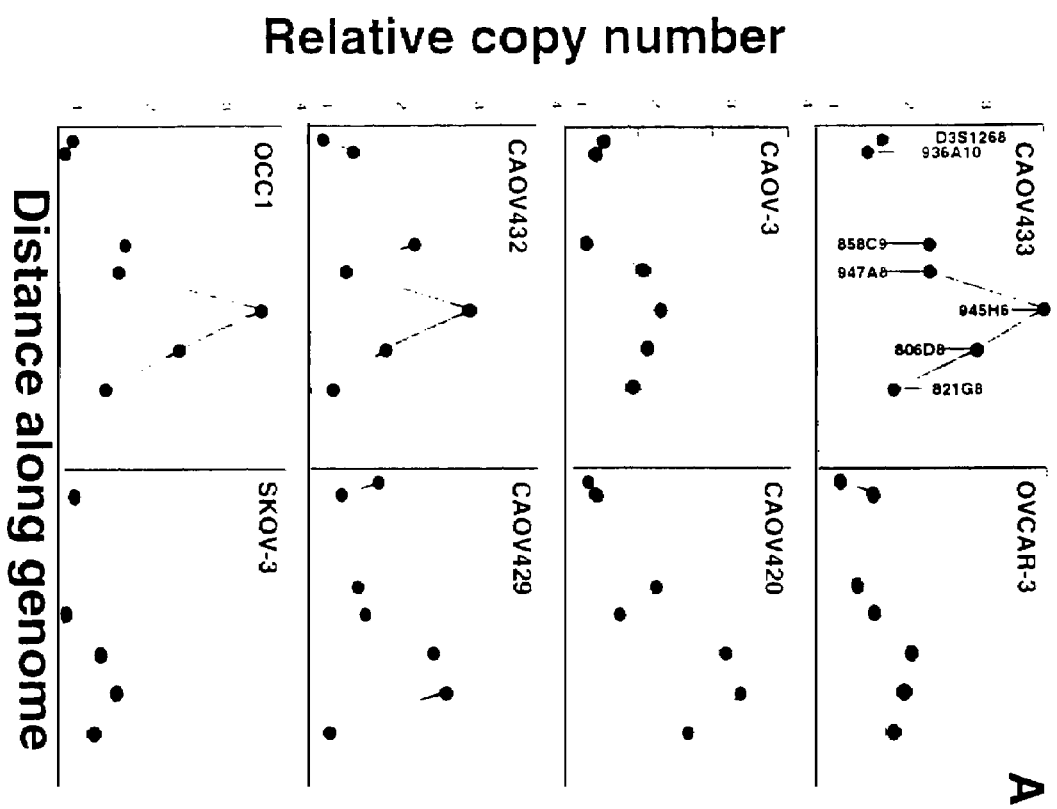
FIGS. 2A-2C show DNA sequence copy number maps generated using dual color FISH with probes generated from YAC or P1 clones shown in FIG. 1. All values shown as the ratio of the number of hybridization signals produced by a test probe to the number of signals produced by a reference probe at D3S1293. Specific probes used for each map are indicated in the upper left panel of each set of maps.
Figure 2B:
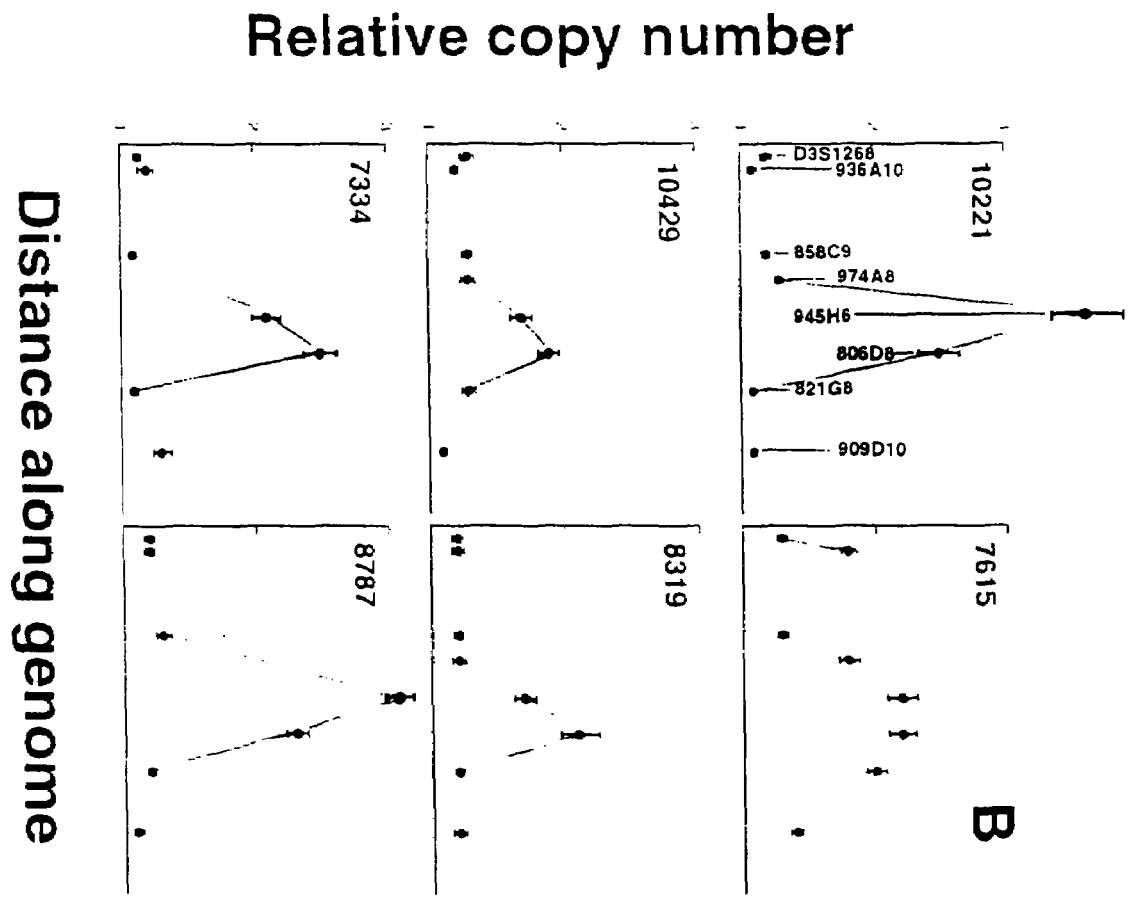
Figure 2C:
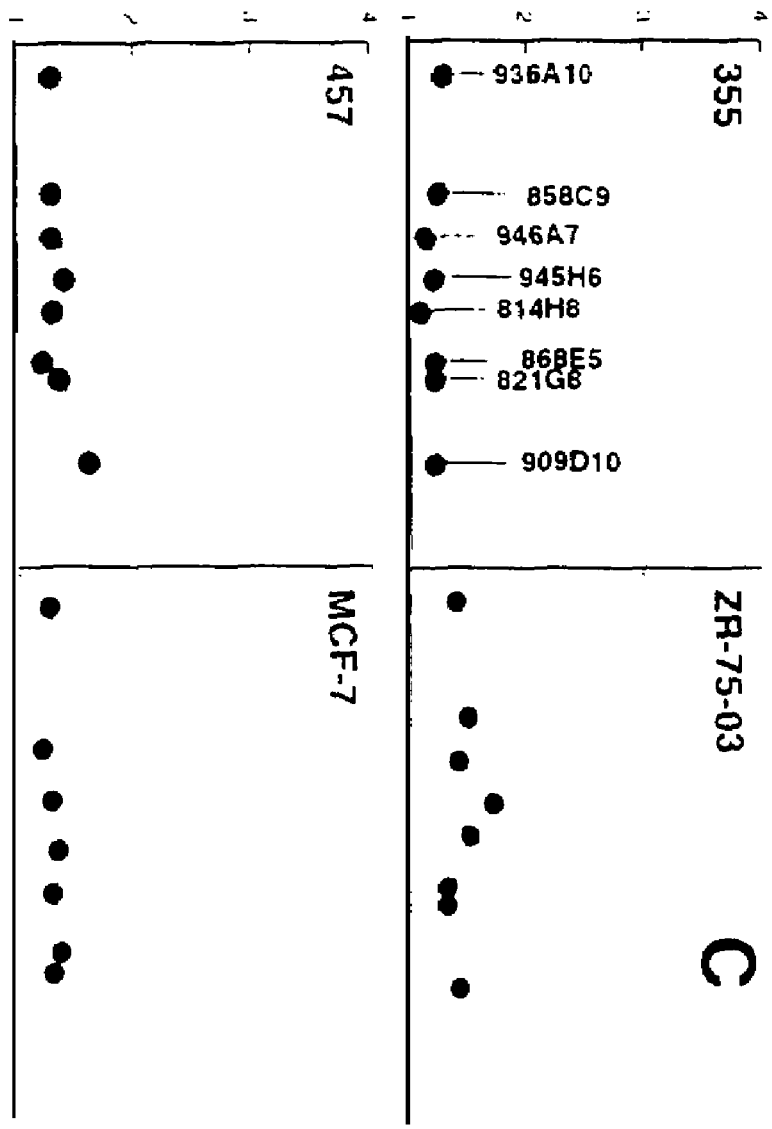

Copy number abnormalities in cancer cell lines for the 3q26 region. CGH studies delineated the region of increase in copy number at best to about 10 Megabases. FISH with well-mapped clones specific to the region was used to refine the region of increase in copy number on 3q26 in ovarian cancer to 2 megabases. FIGS. 2A-2C show the data from hybridization experiments onto ovarian, breast, and melanoma cell lines. The graphs are relative copy numbers of the probes in the cell lines as a function of probe distance along the chromosome. One P1 clone, Glut2, and 5 YAC clones that share sequences with this P1 (683F10, 784H12, 806D8, 822G9, 945H6) consistently show increases in copy number in all ovarian cell lines. A minimal region of increased copy number was defined by YACs 806D6 and 945H6. FISH to the ovarian cell lines using these and other overlapping YAC and P1 clones produced 2 to 4 times more hybridization signals than a reference probe at 3p25 carrying the STS D3S1293. The region of highest copy number typically did not extend outside the region defined by these two YACs (FIG. 2A). OVCAR3 shows a larger region of amplification throughout the region, with the aforementioned clones still manifesting the largest increase in copy number. Breast cancer lines ZR75-30 and MCF-7 showed a smaller increase in copy number for the same clones in the region, and melanoma lines 355 and 457 failed to show increases in copy number in this region (FIG. 2C).

Copy number abnormalities in ovarian tumor samples. All paraffin-embedded ovarian tumor samples also show the same regions of increase in copy umber that were seen in the ovarian cancer cell lines. As seen from Figure, the region of increase in copy number is better defined in the tumor samples, with a sharp increase in the relative copy number for the P1 and its associated YACS. Increases in copy number for tumor sample 595-7615 seem to involve a larger amplicon, as all the probes tested in this tumor show a relatively elevated copy number.

Based on the FISH results of tumor samples and cell lines, we have delineated the critical region of increase in copy number in ovarian cancer on the long arm of chromosome 3 to the region of 3q26.3, spanning one P1 and 5 YACs that share sequences with this P1.

A search of the Unigene and Genome Databases in the critical region revealed 2 known genes, glucose transporter 2 (GLUT2) and phosphatidylinositol 3-kinase, catalytic alpha polypeptide (PIK3CA). Other genes including, protein L22 (RPL22), ectropic viral integration site 1 (EVI1), Cornelia De Lange Syndrome (CDL), butyrylcholinesterase (BCHE), epithelial cell transforming sequence 2 (ECT2), Friend murine leukemia virus integration site 1 homologue (FIM1), and myelodysplasia syndrome 1 (MDS1) map near to but outside the critical region of increased copy number (FIG. 1). The RNA component of the telomerase, HTR, maps to the distal edge of the critical and has been suggested as a candidate gene selected for by copy number increase in this area (Soder et al. *Oncogene* 14:1013-1021 (1997). This gene was mapped to YAC 821G8 by PCR using primers to HTR. The region targeted by this YAC is present in increased copy number in one of the six tumors ans in 4 of 8 ovarian cancer cell lines.

Example 2

This example shows that PIK3CA expression is increased in ovarian cancers as a result of the PIK3CA copy number increase.

As noted above. PIK3CA is an attractive as a candidate oncogene in ovarian cancer because of the broad range of cellular functions that are modulated by increased PI3-kinase activity (Cantley et al. *J. Am. Soc. Nephrol.* 5:1872-1881 (1995), Fry *Biochi. Biophys. Acta* 1226:237-268 (1994)). These include increased including cell proliferation, accelarated glucose transport and catabolism (Frevert et al. *Mol Cell Biol* 117:190-198 (1997), Tsakiridis et al., *Endocrinology* 136:4315-4322 (1995), altered cell adhesion (Chen et al. *J. Biol Chem.* 269:31229-31233 (1994), Kinashi et al. *Blood* 86:2086-2090 (1995)) and altered vesicle transport (Joly et al. *J. Biol. Chem.* 270:13225-13230 (1995) and Dudek et al. *Science* 275:661-665 (1997)).

Increased PI-kinase activity also is implicated in abrogating apoptosis. For example, neuronal survival is increased after activation of PI-kinase by treatment with IGF1 ((Franke et al, *Cell* 88:435-437 (1997), c-myc induced apoptosis is decreased in fibroblasts after activation of the downstream Akt (Kauffmann-Zeh et al. *Nature* 385:544-548 (1997)), survival is decreased in cisplatin-treated ovarian cancer cells after treatment with rapamycin (Shi et al. *Cancer Research* 55:982-1988 (1995)) and survival is increased in MDCK cells detached from the extracellular matrix after activation of Akt (Khwaja et al. *EMBO J.* 16:2783-2793 (1997)). Observations linking PI-kinase activity more directly to cancer include association of the PI-kinase pathway with the ras and wnt signaling pathways (both known to be disregulated by genetic aberrations in human cancers) and demonstration that c-p3k, an avian homolog of PIK3CA is a potent transforming gene in cultured chicken embryo fibroblasts (Chang et al. *Science* 276:1848-1850 (1997)). In addition, Akt2, a homolog of the downstream PI-kinase effector Akt, has been found to be amplified in ~15% of ovarian cancers (Cheng et al. *Proc Natl Acad Sci USA* 89: 9267-71 (1992)).

Experiments were performed to determine whether PIK3CA expression and OI3-kinase activity are increased in ovarian cancers as a result of the PIK3CA copy number increase. Expression of the PIK3CA subunit of PI3-kinase was assessed by Western blot analysis in cancer cell lines and normal epithelia cells. Ovarian cancer cell lines and breast cancer cell lines were cultured in RPMI 1640 medium with 10% fetal bovine serum (FBS). Normal ovarian surface epithelia cells (NOE) were isolated from fresh normal ovarian biopsy specimens and cultured in medium 199 with Earle's salt and MCDB105 (1:1 ratio) plus 15% FBS and 10 ng/ml of EGF. Tumor cells (ASC) were purified from ascites of ovarian cancer patients using density gradients and negative selection with CD45 immunomagnetic beads. Cells were lysed in 1% NP-40 lysis buffer (50 mM Hepes, pH7.4, 150 mM NaCl, 50 mM ZnCl2, 50 mM NaH2PO4, 50 mM NaF, 2 mM EDTA, 1 mM Na3VO4, 2 mM PMSF, 10 mg/ml of aprotinin). Protein concentration of the cell lysates were determined by BCA protein assay subjected to immunoprecipitation with 2 mg of goat polyclonal antibody against the amino terminus of PIK3CA (Santa Cruz Biotechnology) and protein G-conjugated sepharose 4B (Pharmacia) for total 3 hour incubation. Immunoprecipitated proteins were separated by 8% SDS PAGE and immunoblotted with a goat antibody to the carboxy terminus of PIK3CA (Santa Cruz Biotechnology). HRP-conjugated donkey anti-goat IgG was used as secondary reagent. The membranes were developed by ECL and exposed to X-ray films.

Figure 3:
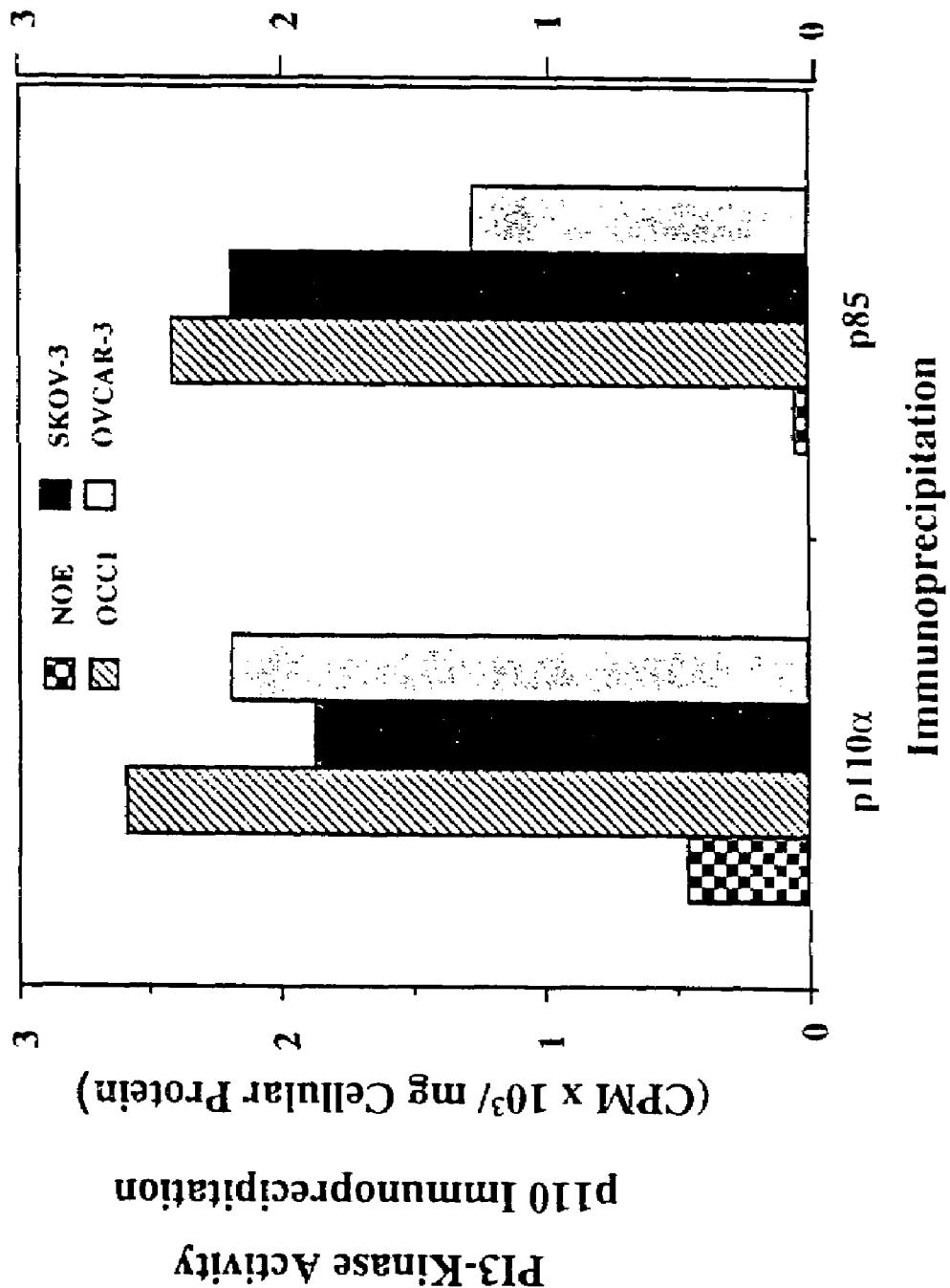
FIG. 3 shows PI3-kinase activity from p11α or p85 immunoprecipitates.

PIK3CA expression relative to normal ovarian epithelial (NOE) cells was assessed in three ovarian cancer cell lines (OVCAR3, OCC11 and SKOV3) and was significantly overexpressed in all three lines. Tumor cells purified from ovarian ascites fluid also overexpressed PIK3CA in 5 of 6 cases. However, PIK3CA was not highly expressed in the breast cancer cell line MDA-MB-453 that did not have increased PIK3CA copy number nor in normal breast epithelial cell lines MCF10F or several other breast cancer cell lines. Immunodepletion experiments with an monoclonal antibody against p85 showed that essentially all PIK3CA protein precipitates with p85 protein in cells in which PIK3CA is overexpressed. The reverse experiment; immunodepletion with an antibody against PIK3CA showed depletion of only about half of all p85 protein. Thus, it is reasonable to expect that overexpression of PIK3CA will lead to increased heterodimer formation and increased PI-kinase activity. This was confirmed by demonstrating that protein immunoprecipitated with an antibody against PIK3CA had increased lipid kinase activity in the three ovarian cancer cell lines relative to NOE (FIG. 3). PI3-kinase activity was assessed in NOE and ovarian cancer cell lines as follows. NOE and ovarian cancer cells were lysed in 1% NP-40 lysis buffer. PI3-kinase was immunoprecipitated from each cell lysate (1 mg of cellular protein) by goat anti-PIK3CA (amino terminus) antibody or rabbit antibody to p85 regulatory subunit of PI3-kinase (upstate Biotechnology, Inc.). The immunoprecipitates were washed sequentially in: a) PBS, 100 mM Na3VO4, 1% Triton X-100; b) 100 mM Tris, pH7.6, 0.5M LiCl, 100 mM Na3VO4; c) 100 mM Tris, pH7.6, 100 mM NaCl, 1 mM EDTA, 100 mM Na3VO4; d) 20 mM Hepes, pH7.5, 50 mM NaCl, 5 mM EDTA, 30 mM NaPPi, 200 mM Na3VO4, 1 mM PMSF, 0.03% Triton X-100. Immunoprecipitates were resuspended in 30 ml kinase reaction buffer (33 mM Tris, pH7.6, 125 mM NaCl, 15 mM MgCl2, 200 mM adenosine, 20 mM ATP, 30 mCi [g-32P]ATP). Phosphatidylinositol (PI) was resuspended in 20 mM Hepes, pH7.5 at 2 mg/ml and sonicated on ice for 10 min. PI3-kinase reaction was initiated by addition of 10 ml of the PI suspension. The reaction proceeded for 30 min at room temperature and was terminated by 200 ml of 1N HCl. Lipids were extracted by 600 ml of chloroform:methanol (1:1). The organic phase was washed with H2O, collected and dried by vacuum centrifugation. The lipids were resuspended in 20 ml of chloroform:methanol (1:1) and resolved on Silica gel G60 thin-layer chromatography (TLC) plates in chloroform:methanol: NH4OH:H2O (60:47:2; 11.3). Radiolabeled phosphatidylinositol phosphate was visualized by autoradiography and then scraped off the plates and quantitated by β-scintillation counting.

Figure 4A:
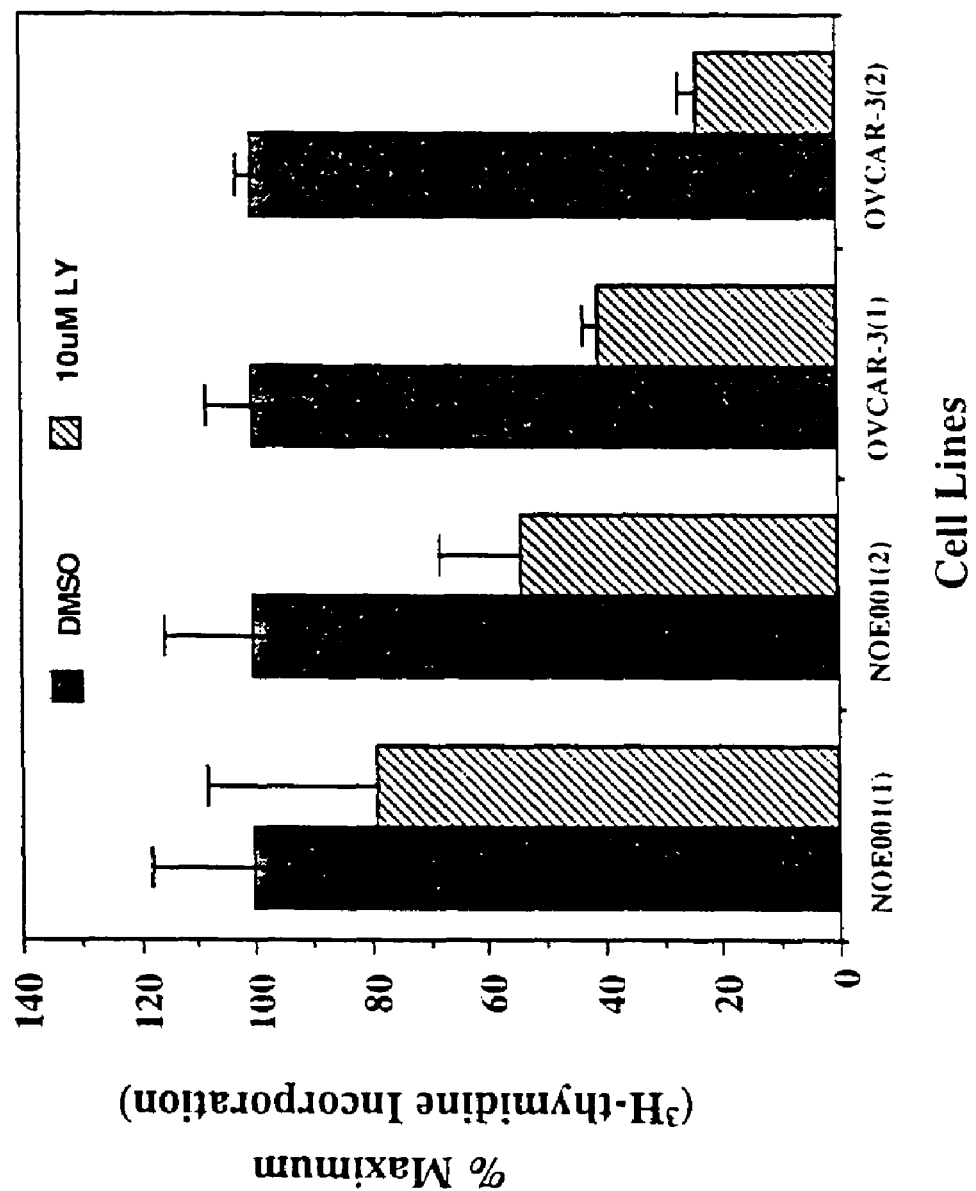
FIGS. 4A and 4B show the effect of inhibition of PI3-kinase activity with LY294002 on proliferation and cell viability. NOE, MCF10F or OVCAR3 (as indicated) were starved of serum overnight and then cultured in 0.5% serum.
Figure 4B:
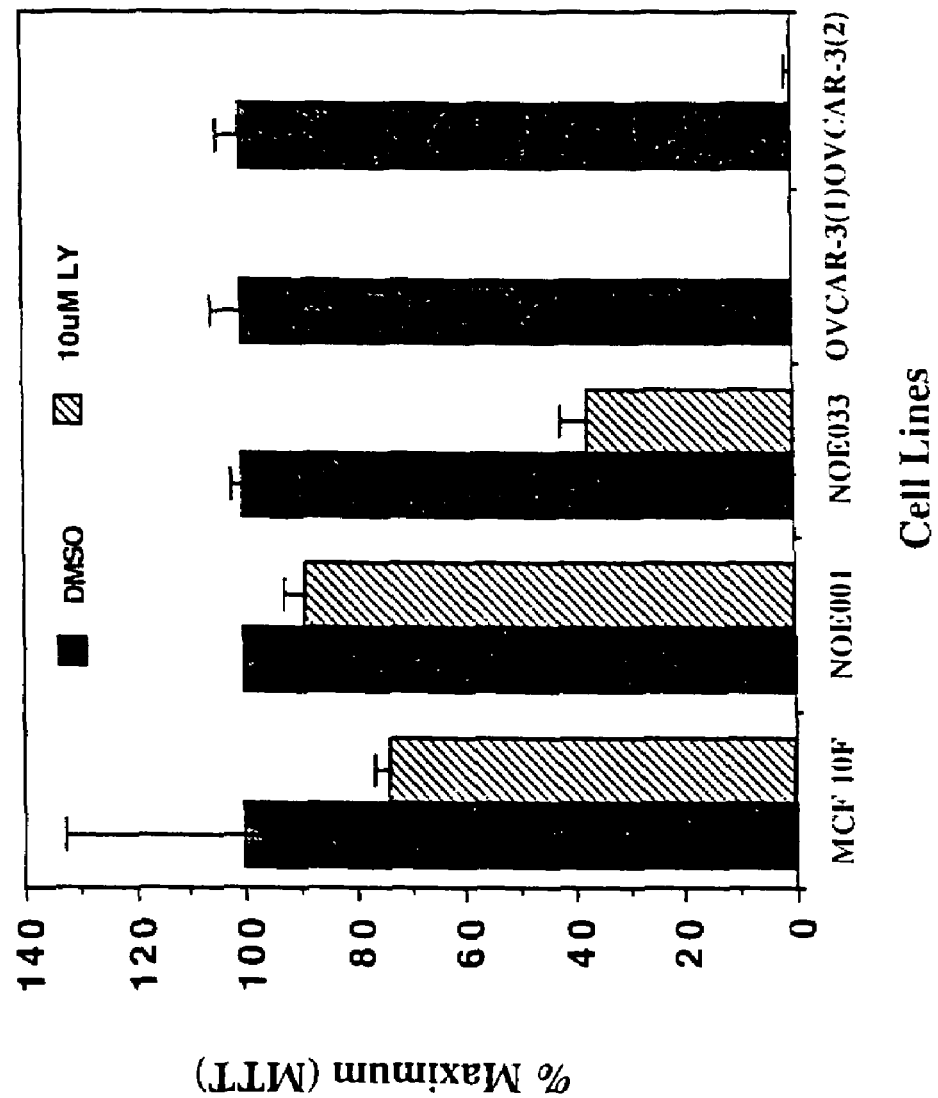

Increased PI-kinase activity might contribute to tumor progression by increasing the rate of cell proliferation and/or increasing cell survival. Incubation of the OVCAR3 ovarian cancer cell line with the specific PI-kinase inhibitor LY294002 induced a marked decrease in cellular proliferation as indicated by thymidine incorporation (FIG. 4a).

Cell proliferation and viability assay was assessed before and after treatment with the PI3-kinase inhibitor LY294002 as follows. Cells were cultured in 96-well plates (15×103 cells/well) and serum starved overnight prior to the addition of LY294002 (Calbiochem) at various concentrations. For thymidine incorporation assay, cells were incubated with LY294002 in the presence of 0.5% DMSO and 0.5% fetal bovine serum for 48 hours followed by another 18 hour incubation with [3H]thymidine (lmCi/well, Amersham). Cells were harvested by 5% TCA and 0.25N NaOH. [3H]thymidine incorporation was measured by b-scintillation counting. Percent Maximum was converted from cpm as: % Maximum=cpm (with LY294002)/cpm (without LY294002)×100. For viability assay, cells were incubated with LY294002 as described above for 96 hours. MTT (25 ml of 5 ml/ml in PBS) was added to each well and incubated at 37° C. for 2 hours. Cells were then lysed by addition of 100 ml lysis buffer (20% SDS in 50% N,N-dimethylformamide, pH4.7). The cultures were set at 37° C. overnight and measured by microplate reader at 570 nm wavelength. Percent Maximum was converted from OD570 as indicated above.

OVCAR3 cells were more sensitive to the effect of LY294002 than NOE (FIG. 5A) or the MCF10A or MCF10F cell lines which had normal PIK3CA copy number and low p110α levels (see above). Strikingly, inhibition of PI-kinase with LY294002 resulted in a marked decrease in viability of OVCAR3 cell as compared to NOE or MCF10F cells as assessed by the ability to convert the MTT dye (FIG. 5B). In fact, OVCAR3 cells were 10 (in the presence of 0.5% FCS) to 100 (in serum free media) times more sensitive to the effect of LY294002. This decrease in viability (FIG. 5B) was associated with an increased rate of programmed cell death at 24 (24% vs 51%) and 48 hour (22% vs 52%) as assessed by a fluorescence based measurement of free DNA ends Apo direct, Phoenix Flow Systems.

Taken together, these studies suggest that increased copy number at 3q26.3 contributes to ovarian cancer genesis and/or progression by increasing PI-kinase activity. The exact mechanism by which this occurs remains unknown since the level of p110α protein increases more than can be accounted for by the 2 to 4-fold increase in copy number. One possibility is that the genomic changes disregulate gene activity by altering regulatory sequences or by disrupting other feed back control mechanisms. However it occurs, PI-kinase activity seems to be increased dramatically relative to NOE in ovarian cancer cell lines and tumors showing increased PIK3CA copy number.

Increasing PI-kinase activity might contribute to tumor development or progression by increasing the rate of cell proliferation (e.g. by activating ras and/or by altering transcription of wnt-1 responsive gene by inhibiting the production of GSK-3 needed for proteolytic degradation of β-catenin (Hopkin *The Journal Of NIH Research* 9:21-23 (1997)). The influence of PI-kinase activity on apoptosis in cells separated from the extracellular matrix may be significant in ovarian cancer because of the strong association between ovarian cancer incidence and number of cycles of ovulation. The disruption of the stromal-epithelial structure, such as occurs during ovulation, has been found to induce genetic aberrations and to be tumorigenic in other model systems. Thus, abrogation of apoptosis by activating PI-kinase might allow genetically damaged cells to survive and to evolve toward a malignant phenotype. This is consistent with our finding that increased copy number at 3q26 is an early event in ovarian cancer.

These associations and the strong inhibition by LY294002 of cell proliferation and survival suggest that therapeutic agents targeting the PI3-kinase pathway may be effective against ovarian cancers. In addition, the presence in the serum of one or more of the proteins in the PI3-kinase pathway also might be diagnostic for the disease since increased copy number at 3q26.2 has been described as an early event in ovarian cancer. This is important since earlier detection of this disease is likely to have a significant impact on patient survival.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A method of inhibiting the pathological proliferation of ovarian cancer cells in a patient, the method comprising:

detecting the presence of an amplification of PIK3CA in ovarian cancer cells from the patient; and administering a therapeutically effective dose of an inhibitor of PI3 kinase to the patient, wherein the inhibitor inhibits PI3 kinase enzymatic activity.

2. The method of claim 1, wherein the inhibitor of PI3 kinase is a non-peptidic inhibitor of PI3 kinase phosphoinositide phosphorylation activity.

3. The method of claim 2, wherein the non-peptidic inhibitor is LY294002.

* * * * *